United States Patent
Meredith et al.

(10) Patent No.: US 10,796,789 B2
(45) Date of Patent: Oct. 6, 2020

(54) METHOD AND APPARATUS FOR INITIATING A MEDICINE CONTROL ACTION

(71) Applicants: AT&T Mobility II LLC, Atlanta, GA (US); AT&T Intellectual Property I, L.P., Atlanta, GA (US)

(72) Inventors: Sheldon Kent Meredith, Roswell, GA (US); William Cottrill, Canton, GA (US)

(73) Assignees: AT&T Mobility II LLC, Atlanta, GA (US); AT&T Intellectual Property I, L.P., Atlanta, GA (US)

( * ) Notice: Subject to any disclaimer, the term of this patent is extended or adjusted under 35 U.S.C. 154(b) by 670 days.

(21) Appl. No.: 14/959,762

(22) Filed: Dec. 4, 2015

(65) Prior Publication Data

US 2017/0161457 A1    Jun. 8, 2017

(51) Int. Cl.
| | |
|---|---|
| *G16H 20/10* | (2018.01) |
| *G16H 40/67* | (2018.01) |
| *G16H 20/00* | (2018.01) |
| *G16H 10/60* | (2018.01) |
| *G16H 40/63* | (2018.01) |

(52) U.S. Cl.
CPC .......... *G16H 20/10* (2018.01); *G16H 20/00* (2018.01); *G16H 40/67* (2018.01); *G16H 10/60* (2018.01); *G16H 40/63* (2018.01)

(58) Field of Classification Search
CPC . G06F 19/3456; G06F 19/3418; G16H 10/60; G16H 40/63; G16H 40/67; G16H 20/00; G16H 20/10
See application file for complete search history.

(56) References Cited

U.S. PATENT DOCUMENTS

| | | | |
|---|---|---|---|
| 6,421,650 B1 | 7/2002 | Goetz et al. |
| 6,909,359 B1 | 6/2005 | McGovern |
| 8,032,397 B2 | 10/2011 | Lawless |
| 8,391,104 B2 | 3/2013 | De la Huerga |
| 8,417,381 B2 | 4/2013 | Vonk et al. |
| 8,538,775 B2 | 9/2013 | Skomra |

(Continued)

FOREIGN PATENT DOCUMENTS

| | | |
|---|---|---|
| CN | 103544369 | 1/2014 |
| WO | WO 2012/011919 | 1/2012 |

(Continued)

OTHER PUBLICATIONS

"RxPense® Mobile App," MediPense®, medipense.com, accessed: Dec. 2015. http://www.medipense.com/en/rxpense-mobile/ Discloses a mobile App and medication monitor. It tracks patients' medications, provides alerts and reminders, monitors adherence.

(Continued)

*Primary Examiner* — Jonathan Durant

(57) ABSTRACT

A method and apparatus for initiating a medicine control action are disclosed. For example, the method implemented via a processor receives at least one picture, the at least one picture comprising an image of one or more pills and a respective prescription bottle of each one of the one or more pills, determines the medicine control action is required in response to the receiving the at least one picture, establishes a data connection with an endpoint device in response to the determining, and initiates the medicine control action over the data connection to the endpoint device.

18 Claims, 3 Drawing Sheets

(56) References Cited

U.S. PATENT DOCUMENTS

| | | | |
|---|---|---|---|
| 8,552,868 | B1 | 10/2013 | Ferguson |
| 8,648,716 | B2 | 2/2014 | Steinmetz |
| 9,008,384 | B2 | 4/2015 | Oh |
| 9,147,163 | B1 | 9/2015 | Nease et al. |
| 2011/0206238 | A1 | 8/2011 | Kinser |
| 2011/0231202 | A1* | 9/2011 | Hanina .................. G06Q 10/10 705/2 |
| 2012/0005222 | A1* | 1/2012 | Bhagwan ................ G06K 9/18 707/769 |
| 2013/0028480 | A1* | 1/2013 | Rothschild ............ G06F 19/326 382/103 |
| 2013/0254966 | A1* | 10/2013 | Pattison ............. A41D 13/1245 2/69 |
| 2014/0180707 | A1 | 6/2014 | Kukreja et al. |
| 2014/0188502 | A1* | 7/2014 | Defrank .............. G06F 19/3462 705/2 |
| 2014/0297329 | A1* | 10/2014 | Rock .................. G06F 19/3456 705/3 |
| 2014/0303989 | A1 | 10/2014 | Ferguson |
| 2015/0088547 | A1 | 3/2015 | Balram et al. |
| 2015/0254427 | A1 | 9/2015 | Burrows et al. |
| 2015/0302175 | A1 | 10/2015 | Hanson et al. |
| 2015/0310185 | A1 | 10/2015 | Shah |
| 2016/0103967 | A1* | 4/2016 | Bulut ..................... G16H 40/63 705/2 |

FOREIGN PATENT DOCUMENTS

| | | |
|---|---|---|
| WO | WO 2012/145789 | 11/2012 |
| WO | WO 2013/033033 | 7/2013 |
| WO | WO 2013/127564 | 9/2013 |
| WO | WO 2014/197774 | 12/2014 |
| WO | WO 2015/131038 | 9/2015 |

OTHER PUBLICATIONS

"Automated Medication Dispenser (AMD)," Illinois Department on Aging, illinois.gov, accessed: Dec. 2015. https://www.illinois.gov/aging/CommunityServices/Pages/Automated-Medication-Dispenser-(AMD).aspx Discloses "a portable, mechanical system that can be programmed to dispense or alert the participant to take non-liquid oral medications in the participant's residence or other temporary residence in Illinois through auditory, visual or voice reminders . . . and supported by a Department approved AMD provider through either the telephone line or a wireless/cellular connection".

"Medication Management Technologies for Long-Term and Post-Acute Care: A Primer and Provider Selection Guide," White Paper, LeadingAge™, leadingage.org, 2015. http://www.leadingage.org/uploadedFiles/Content/Centers/CAST/Resources/Medication%20ManagementWhitepaper.pdf White paper discloses range of medication management technologies available in the marketplace, their uses, and the benefits of their use.

Fong, B., K. F. Tsang, and C. K. Li, "Personalized Elderly Assistive Home Care Using 3G Networks," Journal of advances in information technology 4.3 (2013): 136-141. http://www.jait.us/uploadfile/2014/1215/20141215113303201.pdf Discloses a system "to promote health awareness among those living alone, issuing condition based reminders and alerts, and continual monitoring for those at risk therefore become an important preventive measure where participants will be able to carry out their daily tasks while enjoying their retirement lives with some peace of mind."

Cole, Bernard, "A pill dispenser that reminds you," embedded, embedded.com, May 20, 2014. http://www.embedded.com/electronics-blogs/cole-bin/4430371/A-pill-dispenser-that-reminds-you Discloses an automated pill dispenser that incorporates wireless M2M, IoT, bluetooth, and mobile phone technologies. The dispenser has compartments that flash when it's time to take the medicine, alarms to remind the patient if he/she has missed a dose; it can send a message via text message, email or phone call.

Lee, Young-Beom, et al. "Pill-ID: Matching and retrieval of drug pill images." Pattern Recognition Letters 33.7 (2012): 904-910. http://www.cse.msu.edu/biometrics/Publications/GeneralBiometrics/LeeParkJain_PILLID_MatchingRetrievalDrugPillImages_PRL11.pdf Discloses "an image based matching tool to automatically identify illicit drug pills based on their imprint, size, shape, color, etc."

* cited by examiner

METHOD AND APPARATUS FOR INITIATING A MEDICINE CONTROL ACTION

The present disclosure relates to a method, computer-readable storage device, and apparatus for initiating a medicine control action.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Medication management, e.g., taking medicine such as pills, can be difficult for individuals, especially as the individuals become older. Generally, as individuals grow older, these elderly individuals may have a plethora of health problems resulting in the need to take a large amount of medications. In addition, these elderly individuals may become more forgetful as they grow older resulting in the potential mismanagement of their prescriptions.

Mismanagement of prescription medicines leads to a large number of fatalities in the United States each year. Many times, these fatalities could be avoided or prevented if there was an automated system to ensure that individuals are taking the proper medications and to ensure that no harmful drug interactions exist between the medications that the individual is taking.

Embodiments of the present disclosure provide a method and system for managing medicines and interactions. In addition, the method and system can automatically initiate a medicine control action based on information that is received from the individual.

Figure 1:
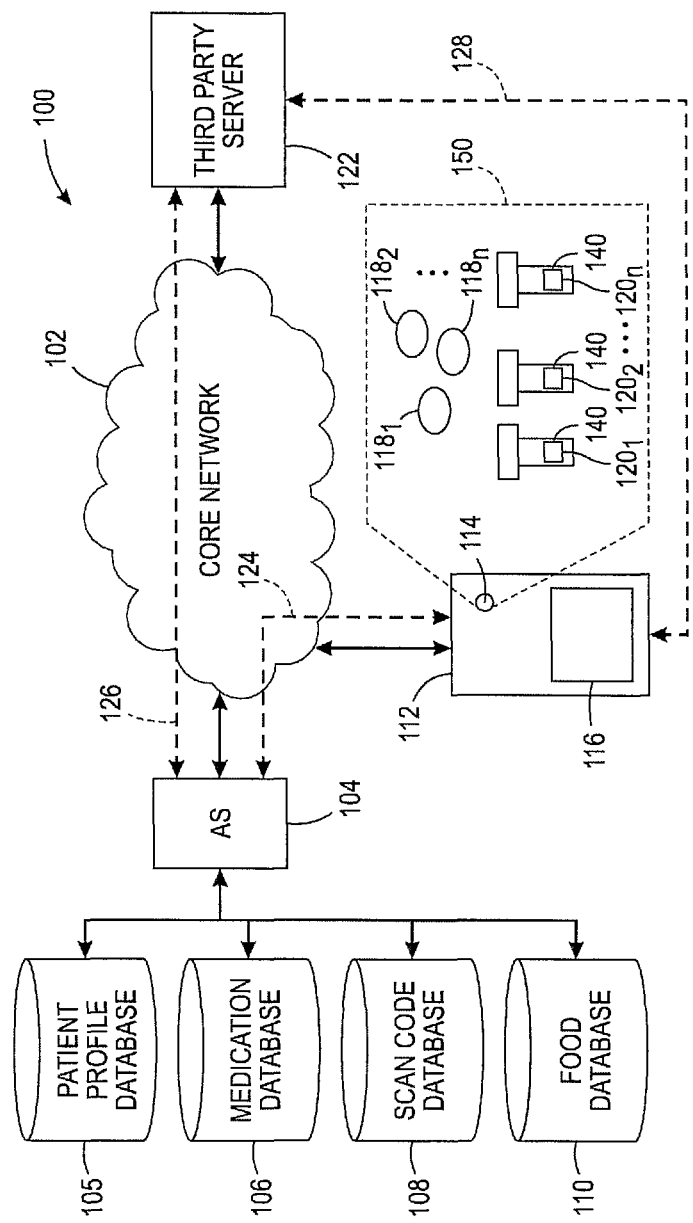
FIG. 1 illustrates an example network related to the present disclosure.

FIG. 1 illustrates an example network 100 related to the present disclosure. In one example, the network 100 has been simplified for ease of explanation. In other words, the network 100 may include additional network elements (not shown), such as gateways, routers, additional access networks, firewalls, switches, and the like. In fact, the network 100 may comprise various access networks. For example, the access networks may comprise a wireless network such as a Wireless-Fidelity (Wi-Fi) network, a cellular network (e.g., 2G, 3G, and the like), a long term evolution (LTE) network, and the like.

In one embodiment, the network 100 may include a core network 102, an application server (AS) 104 (e.g., a database server) and one or more databases (DBs) 105, 106, 108 and 110. The core network 102 may comprise any type of communications network, such as for example, a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, or a wireless network. It should be noted that an IP network is broadly defined as a network that uses Internet Protocol to exchange data packets. Although only a single AS 104 and four DBs 105, 106, 108 and 110 are illustrated in FIG. 1, it should be noted that any number of application servers and databases may be deployed. Furthermore, in one embodiment, the AS 104 and the DBs 105, 106, 108 and 110 are deployed within the core network 102 and are operated by the a network service provider to provide a medication management service, e.g., to initiate a medicine control action as discussed below.

In one embodiment, the DB 105 may also be referred to as the patient profile DB 105. For example, the patient profile DB 105 may include profiles of various individuals that have elected to subscribe to the medicine management service. For example, individuals may decide to subscribe to the medicine management service to have the AS 104 automatically track and manage the individual's prescribed medicines. In other words, patient information may not be stored in the patient profile DB 105 unless the patient has agreed to the medicine management services accessing private information associated with the individual. In other words, the patient (e.g., a subscriber of a communications network service) will opt-in to the medicine management services in order for the network service provider to gain access to the private information associated with the individual. In one embodiment, the patient profile may include a name of the individual, an age of the individual, a history of health records, current prescriptions of the individual, known allergies of the individual, and the like.

In one embodiment, the DB 106 may also be referred to as a medication DB 106. For example, the medication DB 106 may include pictures of different types of medicines such as pills. The pictures may be used to identify or verify that the individual is taking the correct medications (e.g., pills $118_1$ to $118_n$). The term "pill" is intended to cover a medication that is embodied in a small globular mass, e.g., a tablet or a capsule of medicinal substance covered with a hard coating, intended to be swallowed by a user. Said another way, a pill is a pellet or tablet of medicine to be taken by a user orally.

In one embodiment, the DB 108 may also be referred to as a scan code DB, e.g., a quick response (QR) code DB and/or a bar code DB. For example, the scan code DB 108 may include information associated with various scannable codes such as QR codes or bar codes that may be found on prescription bottles (e.g., $120_1$-$120_n$). In one example, the scan code DB 108 may be used to determine whether any harmful drug interactions may exist between the pills $118_1$-$118_n$ that the individual is taking.

In one embodiment, the DB 110 may also be referred to as a food DB 110. The food DB 110 may include information about the effects of various types of food items with various types of medications. For example, certain food items may have a harmful interaction with certain types of medications, e.g., grapefruit juice may negatively affect cholesterol medications, bananas may negatively affect blood pressure regulating medications, milk may negatively affect certain types of antibiotics, walnuts may negatively affect thyroid medications, leafy greens such as kale, broccoli and spinach may negatively affect blood thinner medications, and so on.

In one embodiment, the network 100 may include a third party server 122. In one example, the third party server 122 may be a database server of a health care service provider (e.g., a doctor and/or a hospital), a pharmacy, and the like, providing a medical service to the individual. In one embodiment, the AS 104 may update one or more of the databases 105, 106, 108 and 110 via information obtained from the third party server 122. The AS 104 may communicate over an Internet Protocol (IP) network 102 and obtain information that can be stored in the appropriate database 105, 106, 108 and/or 110. For example, the AS 104 may download a database of images of various medications (e.g., pictures of pills) or a description of all available medications from the third party server 122 to be stored in the medication DB 106. In another example, the AS 104 may download patient profiles of subscribing individuals from the third party server 122 of the health care provider to be stored in the patient profile DB 105, and so forth.

In one embodiment, the network 100 may include a mobile endpoint device 112, e.g., a mobile cellular phone or a smartphone. The mobile endpoint device 112 may be any type of mobile endpoint device having a camera 114 that can communicate over a network, e.g., the IP network 102, via a wired or wireless connection. For example, the mobile endpoint device 112 may be a smartphone, a tablet computer, a laptop computer, and the like.

In one embodiment, individuals that elect to subscribe to the medicine management services may download an application 116 that can be executed on the mobile endpoint device 112. The embodiments of the present disclosure can be executed by the AS 104 or locally by the mobile endpoint device 112.

In one embodiment, the mobile endpoint device 112 can capture at least one picture 150 (e.g., one or more pictures) via the camera 114 of the pills $118_1$-$118_n$ (herein referred to individually as a pill 118 or collectively as pills 118) and prescription bottles $120_1$-$120_n$ (herein referred to individually as a prescription bottle 120 or collectively as prescription bottles 120). The at least one picture 150 having an image of the one or pills and the respective prescription bottle(s) may be processed locally by the mobile endpoint device 112 or the AS 104.

In one embodiment, the AS 104 may perform the medicine management services and initiate the medicine control action. For example, the AS 104 may be a dedicated device having a processor to execute instructions stored in memory of the AS 104 to perform the functions described herein.

For example, the picture 150 may be transmitted to the AS 104 over the IP network 102. In one embodiment, the AS 104 may process the image 150. For example, the prescription bottles 120 may include a QR code 140. The QR code 140 may be found in the scan code DB 108 to determine the type of medication, dosage information, and the like, for the pill contained in the respective prescription bottles $120_1$ to $120_n$. In another embodiment, if the prescription bottles 120 do not have a QR code 140, then an optical character recognition (OCR) program may be used to read the labels on the prescription bottles 120, i.e., to provide text information located on the prescription bottles.

In one example, the AS 104 may further verify that no harmful drug interactions exists between the pills 118 associated with the prescription bottles 120 based on the information stored in the scan code DB 108. In addition, the AS 104 may verify that the correct individual is taking the pills 118. For example, when the individual takes the picture 150, the individual may log into the AS 104 via the application 116. Thus, the AS 104 may know who has logged in and compare the name on the prescription bottles 120 with the name of the user that logged into the application 116 used to transmit the picture 150.

In addition, in one example the AS 104 may further verify that no incorrect prescriptions that the individual is allergic to have been prescribed to the individual. For example, based on the name of the user that logged into the AS 104 via the application 116, the AS 104 may obtain the patient profile associated with the individual from the patient profile DB 105. The patient profile of the individual may include known allergies to various medicines for the individual, certain brands that produce side effects for the individual, and the like.

Based on the pills that are intended to be stored in the prescription bottles $120_1$ to $120_n$, the AS 104 may look up images and/or descriptions of the pills in the medication DB 106. Different types of pills 118 may have different shapes, sizes, colors, codes placed on the pill itself (e.g., alphanumeric characters) and the like. The AS 104 may compare the stored image(s) for each type of pill that is supposed to be contained in the prescription bottles $120_1$ to $120_n$ to the images of the pills 118 in the picture 150 to verify that the correct pills are present. For example, the images of the pills 118 may be compared to the images and descriptions of different types of pills stored in the medication DB 106.

In addition, the camera 114 may be used to take pictures of foods that the individual are about to eat. In another embodiment, the individual can take pictures of QR codes on menus associated with food items that the individual has ordered. In another embodiment, the individual may enter the foods into the application 116 that he or she is about to consume. The AS 104 may compare the food items to the food items and associated information stored in the food DB 110 to ensure that the food items do not cause a harmful interaction with the pills 118 that the individual is taking.

In one embodiment, the AS 104 may be used to remind the individual or ensure that the individual has taken his or her medication. For example, based on the patient profile and prescription information obtained from the picture 150, the AS 104 may know a frequency of the dosage (e.g., taking pill $118_1$ twice a day after each meal, taking two pills $118_2$ three times a day every six hours, and so forth). The AS 104 may track how many pills 118 and how often the individual has taken each pill 118 based on the pictures 150 that the AS 104 receives, e.g., analyzing the images of the pills and the associated time stamps that the images are received. This will allow AS 104 to determine what medications and the timing that these medications are being taken by the individual who sent the images.

In one embodiment, if any incorrect prescriptions are prescribed, any harmful interactions exist, the individual has forgotten to take a pill, or any other problem is detected, the AS 104 may initiate a medicine control action. For example, the AS 104 may generate a warning message that may include that an incorrect prescription has been prescribed, that a harmful interaction has been detected, that an incorrect dosage or a wrong type of pills is about to be consumed, a reminder that the individual has forgotten to take a particular pill 118, and the like, and transmit the warning message to the third party server 122 and/or the mobile endpoint device 112. This notification will allow the patient and/or medical professionals providing medical care to the patient to be quickly warned of potential problems relating to the patient's taking of the prescribed medications. In one embodiment, a caregiver, e.g., a family member or a guardian, is also notified, e.g., the warning message is also sent to an endpoint device (e.g., a smartphone or a computer) of the caregiver.

For example, initiation of the medicine control action may cause the AS 104 to establish a data connection 124 with the mobile endpoint device 112 and/or a data connection 126 with the third party server 122. The warning message may be transmitted over the data connection 124 or the data connection 126. The warning message may be displayed to the individual via the mobile endpoint device 112, to a health care provider via the third party server 122, and/or to an endpoint device of the caregiver.

In one embodiment, the medicine control action may be a control signal causing the third party server 122 to establish a communication connection 128 with the mobile endpoint device 112, or vice versa. For example, if the harmful drug interaction has been detected and it appears imminent that the individual is about to consume the pills 118, the AS 104 may send a control signal to the third party server 122 to immediately call the mobile endpoint device 112 to have a health care service provider speak to the individual to ensure that the individual will not take the pills. For example, the medicine management service may require that each patient takes a picture of prescribed medications that the patient intends to take within a next predefined time period, e.g., within the next 5 minutes. In other words, the patient must wait a predefined period of time (e.g., 1 minute, 5 minutes, 10 minutes, or 15 minutes) before taking the medications. This will allow the medicine management service to verify the medications and/or to initiate any medicine control actions. In one example, the telephone call can be initiated by an interactive voice response (IVR) system informing the individual of the detected medication problem. Some users may be more responsive to a medicine control action that requires the users to answer a telephone call speaking to a live person or simply listening to a recorded warning message.

In another embodiment, a medicine control action may be an order to refill a prescription. For example, the AS 104 may automatically track a number of pills 118 for each prescription bottle 120. When a prescription is started, the user may enter the prescription in the application 116, or the number of pills, dosage, and the like, may be obtained from the picture 150. The AS 104 may track a number of pills 118 that are taken in each picture 150 and maintain a total number of pills 118 that should be remaining for a respective prescription bottle 120. The AS 104 may verify in the patient profile DB 105, or on the QR code 140 of the prescription bottle, that the individual has refills remaining. If the individual has refills remaining, the AS 104 may establish a data connection 126 to a third party server 122 of the pharmacy and place an order for a refill. The AS 104 may then establish a data connection 124 to the mobile endpoint device 112 and notify the individual that the refill has been ordered. Subsequently, the third party server 122 may establish a communication connection 128 with the mobile endpoint device 112 to notify the individual that the refill is ready for pick-up.

In one embodiment, the medicine control action may be encrypted for privacy. For example, an encryption key (e.g., a user selected password) may be selected by the individual and the application 116 may provide the encryption key to the AS 104 that can be used to encrypt the medicine control action. However, it should be noted that any encryption methods may be used.

In one embodiment, the medicine control action may be related to a warning message (a text message and/or an audible message, e.g., text-to-speech message) that the individual has forgotten to take a pill. In one embodiment, the AS 104 may send a control signal to the application 116 that causes the application 116 to lock or "impede" various functionalities of the mobile endpoint device 112 except for the application 116 and the camera 114 until a picture 150 of the pills 118 and the prescription bottles 120 is received. Emergency calling functionalities will not be disabled. Impediments may comprise displaying the warning message repeatedly before other functionalities can be used by the patient, e.g., displaying the warning message before allowing the patient to access the Internet, displaying the warning message before allowing the patient to make a phone call, displaying the warning message before allowing the patient to download a file, displaying the warning message before allowing the patient to access an application of the mobile endpoint device, and so on. In other words, a simple warning message may be insufficient for some users, i.e., some users may need a more persistent method of reminding so that the users will take the proper medications.

As noted above, the mobile endpoint device 112 may also perform the initiation of the medicine control action described above. For example, the mobile endpoint device 112 may locally process and analyze the contents of the picture 150.

For example, the mobile endpoint device 112 may not have the same amount of processing capability and memory as the AS 104. As a result, to maximize the efficiency of the application 116 on the mobile endpoint device 112, the mobile endpoint device 112 may download only information from the medication DB 106, the scan code DB 108, and the food DB 110 that is relevant to the individual. For example, only images of pills, or QR codes associated with the prescription bottles 120, that the individual has taken or is prescribed may be downloaded from the medication DB 106 and the scan code DB 108 to the mobile endpoint device 112.

Figure 2:
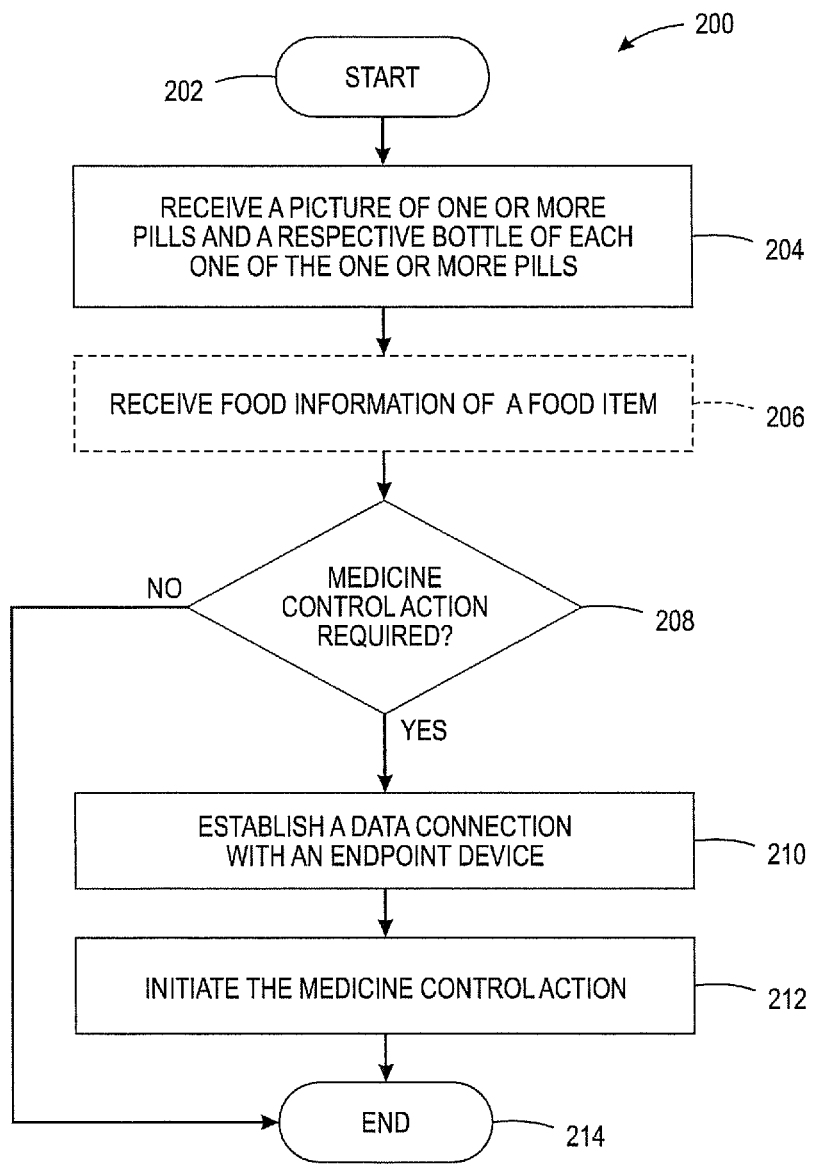
FIG. 2 illustrates a flowchart of an example method of the present disclosure for initiating a medicine control action.

FIG. 2 illustrates a flowchart of an example method 200 of the present disclosure for transmitting a medicine control action. In one embodiment, the method 200 may be implemented by the AS 104 dedicated for performing the functions described herein, the mobile endpoint device 112, or the computer or processor as described in FIG. 3.

At step 202, the method 200 begins. At step 204, the method 200 receives at least one picture (e.g., one or more pictures) of one or more pills or and a respective bottle of each one of the one or more pills. For example, the each pill may have a prescription bottle that is associated with the pill. In one embodiment, each bottle may have a scan code, e.g., a QR code, on the label of the prescription bottle. In one embodiment, a camera of the mobile endpoint device may take the picture of the pill(s) and the associated prescription bottle(s). In one embodiment, a single picture captures both the pill(s) and the associated bottle(s). In another embodiment, a first picture captures the pill(s) and a second picture captures the associated bottle(s), and so on.

At optional step 206, the method 200 may receive food information of a food item. For example, if the individual is about to eat certain food items and is concerned that the pills may have a harmful interaction with the food items, then the individual may provide the food information. The food information may be provided via a scan code, e.g., a QR code, on a menu if the individual is at a restaurant. In another example, the food information may be provided via a picture. In yet another example, the individual may provide the food information manually via a medicine management service application being executed on the mobile endpoint device of the individual, e.g., the medicine management service application may already have a listing of food items that the individual can select for reporting to the AS 104. For example, the medicine management service application may illustrate pictures that are representative of various food items to be selected, e.g., a set of fruit items, a set of vegetable items, a set of seafood items, a set of animal meat or protein items, a set of various drinks, and so on.

At step 208, the method 200 may determine whether a medicine control action is required. For example, as described above, a picture may be used to analyze the pills and the information associated with the pills found on the bottles. For example, the information on the bottle obtained via an OCR program or a QR code may be compared to a scan code database to identify the pills and determine whether any harmful interactions may occur if the pills (e.g., captured in the picture or image taken by the camera) are mixed or taken together.

The identification of the pills may allow the description or an image of the pills to be found from a medication database. The image of the pills and the pills in the picture may be compared to verify that the correct pills are present based on the information on the bottles. In addition, the dosage information may be verified from the picture. For example, the picture may be analyzed to determine whether the individual is taking the correct pills and the correct number of each type of pills. For example, an elderly patient may remember the type of medications to take, but may forget or may be confused as to the number of each medication to take.

In one embodiment, the medicine allergies of the individual may be obtained from a patient profile of the individual obtained from a patient profile database. The picture may be analyzed to verify that individual is not allergic to any of the pills.

In one embodiment, the food information and the picture may be analyzed to ensure that no harmful interaction will occur if the food item is consumed with the pills. For example, the food information may be compared to information in a food database to identify any harmful interactions.

In one embodiment, the amount of pills in each bottle may be tracked to determine whether a refill order should be placed. For example, the total number of pills in the bottle may be provided when a new bottle is detected in the picture. The total number of pills may be read from the label or the QR code. After each picture, the number of pills in the picture may be tracked and when the total number of pills falls below a threshold, a refill order may be automatically placed.

At step 210, the method 200 may establish a data connection with an endpoint. For example, if the AS is performing the method 200, the AS may establish a data connection with the mobile endpoint device and/or a third party server. Alternatively, if the mobile endpoint device is performing the method 200, the mobile endpoint device may establish a data connection with the third party server 122 or the AS 104.

At step 212, the method 200 initiates the medicine control action. For example, the medicine control action may comprise a warning message being transmitted due to any condition described above that includes the particular harmful interaction, the problem with the particular pill, the automatic refill order, and the like. In one embodiment, the medicine control action may be encrypted for privacy, e.g., the warning message is encrypted. In another example, the medicine control action may comprise a telephone call being initiated by a medical professional, a caregiver and/or an interactive voice response (IVR) system. At step 214, the method 200 ends.

In addition, although not specifically specified, one or more steps, functions or operations of method 200 may include a storing, displaying and/or outputting step as required for a particular application. In other words, any data, records, fields, and/or intermediate results discussed in the method can be stored, displayed and/or outputted either on the device executing the method or to another device, as required for a particular application.

Furthermore, steps, blocks, functions or operations in FIG. 2 that recite a determining operation or involve a decision do not necessarily require that both branches of the determining operation be practiced. In other words, one of the branches of the determining operation can be deemed as an optional step. Moreover, steps, blocks, functions or operations of the above described method 200 can be combined, separated, and/or performed in a different order from that described above, without departing from the example embodiments of the present disclosure.

In one example, the present method for initiating a medicine control action of the present disclosure is implemented via a dedicated database server. Furthermore, in one embodiment, the present method for initiating a medicine control action can be provided in the dedicated database server, e.g., AS 104, operated and managed by a network service provider. For example, the network service provider may operate one or more communications networks to provide one or more services such as telephony services, cellular services, data services (e.g., data access and transfer services, Internet access services, and the like), multimedia delivery services (e.g., multimedia programming delivery services such as movies, videos, music and the like), and the like.

As such, the present disclosure provides at least one advancement in the technical field of medication management for a user. This advancement improves medication adherence by providing a timely medicine control action to a user and/or medical professional to ensure that the proper medication is taken by the user through the use of an image capturing device.

Figure 3:
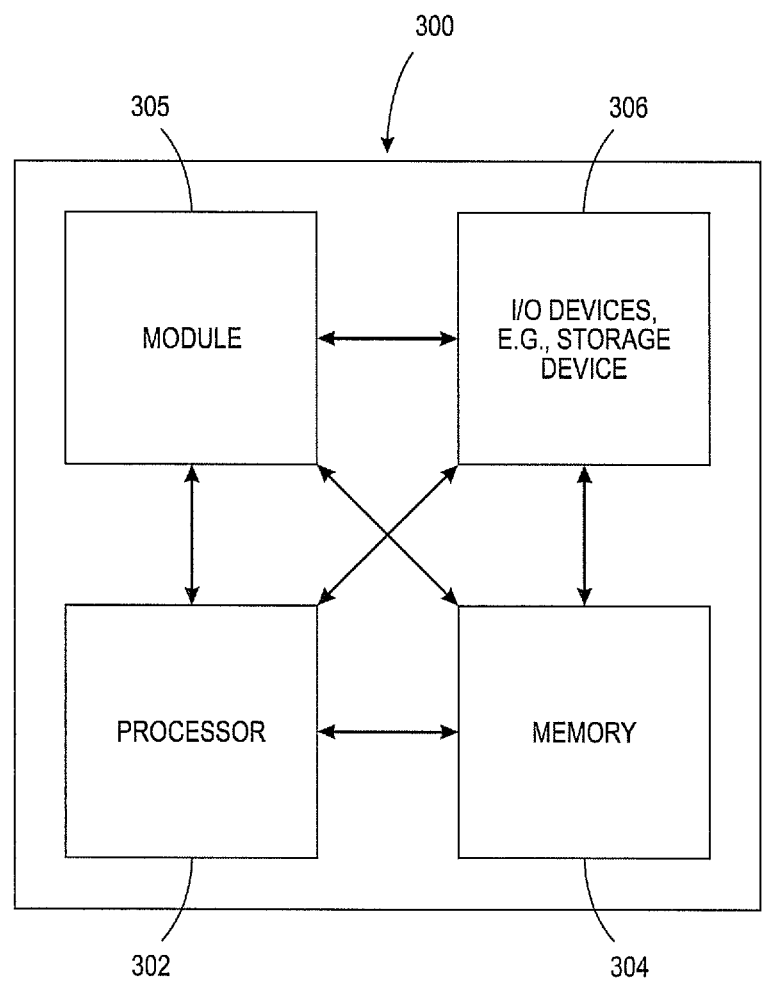
FIG. 3 depicts a high-level block diagram of a computer suitable for use in performing the functions described herein.

FIG. 3 depicts a high-level block diagram of a computer suitable for use in performing the functions described herein. As depicted in FIG. 3, the system 300 comprises one or more hardware processor elements 302 (e.g., a central processing unit (CPU), a microprocessor, or a multi-core processor), a memory 304, e.g., random access memory (RAM) and/or read only memory (ROM), a module 305 for initiating a medicine control action, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computer may employ a plurality of processor elements. Furthermore, although only one computer is shown in the figure, if the method 200 as discussed above is implemented in a distributed or parallel manner for a particular illustrative example, i.e., the steps of the above method 200, or the entire method 200 is implemented across multiple or parallel computers, then the computer of this figure is intended to represent each of those multiple computers.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computer or any other hardware equivalents, e.g., computer readable instructions pertaining to the method(s) discussed above can be used to configure a hardware processor to perform the steps, functions and/or operations of the above disclosed method. In one embodiment, instructions and data for the present module or process 305 for initiating a medicine control action (e.g., a software program comprising computer-executable instructions) can be loaded into memory 304 and executed by hardware processor element 302 to implement the steps, functions or operations as discussed above in connection with the illustrative method 200. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 305 for initiating a medicine control action (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. A method for initiating a medicine control action, the method comprising:
   transmitting, by a processor deployed in a communication network, a first control signal to cause an endpoint device to disable at least one functionality of the endpoint device, wherein the first control signal is transmitted in accordance with a pill consumption schedule of a user of the endpoint device;
   receiving, by the processor from the endpoint device, at least one picture, the at least one picture comprising an image of one or more pills and an image of a respective prescription bottle of each one of the one or more pills;
   receiving, by the processor from the endpoint device, food information of a food item;
   determining, by the processor, the medicine control action is required in response to the receiving the at least one picture and the receiving the food information, wherein the determining comprises:
      identifying the one or more pills in the at least one picture via a medication database; and
      comparing the food information to information in a food database to identify a negative interaction between the food item and the one or more pills;
   establishing, by the processor, a data connection with the endpoint device in response to the determining;
   initiating, by the processor, the medicine control action over the data connection to the endpoint device, wherein the medicine control action comprises a warning message sent to the endpoint device indicating that the food item has the negative interaction with the one or more pills; and
   transmitting, by the processor, a second control signal to cause the endpoint device to enable the at least one functionality of the endpoint device.

2. The method of claim 1, wherein the determining further comprises:
   comparing, by the processor, the one or more pills to a pharmaceutical database to identify whether a drug interaction problem exists.

3. The method of claim 2, wherein the medicine control action further comprises a warning message to the endpoint device to notify the user of the drug interaction problem.

4. The method of claim 1, wherein the medicine control action further comprises a prescription refill order based on a number of pills of the one or more pills falling below a refill threshold based on the at least one picture.

5. The method of claim 1, wherein the medicine control action further comprises a warning message sent to the endpoint device indicating that there is a problem related to a wrong type of pill or a wrong dosage based on the at least one picture.

6. The method of claim 1, wherein the respective bottle includes a scan code used to identify the one or more pills based upon a comparison to a scan code database.

7. A non-transitory computer-readable storage device storing a plurality of instructions which, when executed by a processor deployed in a communication network, cause the processor to perform operations for initiating a medicine control action, the operations comprising:
   transmitting a first control signal to cause an endpoint device to disable at least one functionality of the endpoint device, wherein the first control signal is transmitted in accordance with a pill consumption schedule of a user of the endpoint device;
   receiving, from the endpoint device, at least one picture, the at least one picture comprising an image of one or more pills and an image of a respective prescription bottle of each one of the one or more pills;
   receiving, from the endpoint device, food information of a food item;
   determining the medicine control action is required in response to the receiving the at least one picture and the receiving the food information, wherein the determining comprises:
      identifying the one or more pills in the at least one picture via a medication database; and
      comparing the food information to information in a food database to identify a negative interaction between the food item and the one or more pills;
   establishing a data connection with the endpoint device in response to the determining;
   initiating the medicine control action over the data connection to the endpoint device, wherein the medicine control action comprises a warning message sent to the endpoint device indicating that the food item has the negative interaction with the one or more pills; and transmitting a second control signal to cause the endpoint device to enable the at least one functionality of the endpoint device.

8. The non-transitory computer-readable storage device of claim 7, wherein the determining further comprises:
comparing the one or more pills to a pharmaceutical database to identify whether a drug interaction problem exists.

9. The non-transitory computer-readable storage device of claim 8, wherein the medicine control action further comprises a warning message to the endpoint device to notify the user of the drug interaction problem.

10. The non-transitory computer-readable storage device of claim 7, wherein the medicine control action further comprises a prescription refill order based on a number of pills of the one or more pills falling below a refill threshold based on the at least one picture.

11. The non-transitory computer-readable storage device of claim 7, wherein the medicine control action further comprises a warning message sent to the endpoint device indicating that there is a problem related to a wrong type of pill or a wrong dosage based on the at least one picture.

12. The non-transitory computer-readable storage device of claim 7, wherein the respective bottle includes a scan code used to identify the one or more pills based upon a comparison to a scan code database.

13. An apparatus for initiating a medicine control action, the apparatus comprising:
a processor deployed in a communication network; and
a computer-readable storage device storing a plurality of instructions which, when executed by the processor, cause the processor to perform operations, the operations comprising:
transmitting a first control signal to cause an endpoint device to disable at least one functionality of the endpoint device, wherein the first control signal is transmitted in accordance with a pill consumption schedule of a user of the endpoint device;
receiving, from the endpoint device, at least one picture, the at least one picture comprising an image of one or more pills and an image of a respective prescription bottle of each one of the one or more pills;
receiving, from the endpoint device, food information of a food item;
determining the medicine control action is required in response to the receiving the at least one picture and the receiving the food information, wherein the determining comprises:
identifying the one or more pills in the at least one picture via a medication database; and
comparing the food information to information in a food database to identify a negative interaction between the food item and the one or more pills;
establishing a data connection with the endpoint device in response to the determining;
initiating the medicine control action over the data connection to the endpoint device, wherein the medicine control action comprises a warning message sent to the endpoint device indicating that the food item has the negative interaction with the one or more pills; and
transmitting a second control signal to cause the endpoint device to enable the at least one functionality of the endpoint device.

14. The apparatus of claim 13, wherein the determining further comprises:
comparing the one or more pills to a pharmaceutical database to identify whether a drug interaction problem exists.

15. The apparatus of claim 14, wherein the medicine control action further comprises a warning message to the endpoint device to notify the user of the drug interaction problem.

16. The apparatus of claim 13, wherein the medicine control action further comprises a prescription refill order based on a number of pills of the one or more pills falling below a refill threshold based on the at least one picture.

17. The apparatus of claim 13, wherein the medicine control action further comprises a warning message sent to the endpoint device indicating that there is a problem related to a wrong type of pill or a wrong dosage based on the at least one picture.

18. The apparatus of claim 13, wherein the respective bottle includes a scan code used to identify the one or more pills based upon a comparison to a scan code database.

* * * * *